US006552511B1

(12) United States Patent
Fayram

(10) Patent No.: US 6,552,511 B1
(45) Date of Patent: Apr. 22, 2003

(54) HYBRID BATTERY NETWORK FOR IMPLANTABLE MEDICAL DEVICE

(75) Inventor: Timothy A. Fayram, Gilroy, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 09/545,044

(22) Filed: Apr. 7, 2000

(51) Int. Cl.[7] .............................................. H02J 7/00
(52) U.S. Cl. ................................................... 320/103
(58) Field of Search ............................... 320/126, 103, 320/107; 607/5

(56) References Cited

U.S. PATENT DOCUMENTS

| | | | |
|---|---|---|---|
| 5,372,605 A | 12/1994 | Adams et al. | 607/5 |
| 5,568,038 A | 10/1996 | Tatsumi | 320/14 |
| 5,674,248 A | 10/1997 | Kroll et al. | 607/5 |
| 5,713,936 A | * 2/1998 | Staub et al. | 324/433 |
| 5,835,185 A | 11/1998 | Kallman et al. | 351/113 |
| 5,919,211 A | * 7/1999 | Adams | 607/5 |
| 5,928,272 A | * 7/1999 | Adkins et al. | 607/45 |
| 5,957,956 A | * 9/1999 | Kroll et al. | 607/5 |
| 5,991,665 A | 11/1999 | Wang et al. | 607/61 |
| 5,998,052 A | 12/1999 | Yamin | 429/9 |
| 6,008,625 A | 12/1999 | Gan et al. | 320/129 |
| 6,038,473 A | * 3/2000 | Olson et al. | 320/116 |

OTHER PUBLICATIONS

Linden, David; Handbook of Batteries; at latest Dec. 1985; McGraw–Hill, Inc.; pp. 41.10, 14.11, and 36.27.*
Estes, III, et al., "Implantable Cardioverter–Defibrillators, A Comprehensive Textbook", Copyright 1994, Mark Dekker, Inc., Chapter 8, Energy Storage and Delivery, pp. 123–132.

Drews, et al., "Development of a Hybrid Battery System for an Implantable Biomedical Device, Especially a Defibrillator/Cardioverter (ICD)", Journal of Power Sources 80, (1999) p. 107–111.

Drews, et al., "High–Rate Lithium/Manganese Dioxide Batteries: the Double Cell Concept", Journal of Power Sources 65, (1997), p. 120–132.

* cited by examiner

Primary Examiner—Gregory J. Toatley, Jr.
(74) Attorney, Agent, or Firm—Steven M. Mitchell

(57) ABSTRACT

An implantable cardiac stimulation device with a hybrid battery network having first and second batteries with different battery chemistries connected in parallel with each other. The first dense cell battery has a higher resistance and greater energy density than the second fast cell battery, and the fast cell battery has greater current carrying capability than the dense cell battery. The dense cell battery has a higher voltage than the fast cell battery. In one embodiment the dense cell is a Lithium Carbon Monofluoride cell and the fast cell is a Lithium Silver Vanadium Oxide cell. During high current demand of high voltage capacitor charging, the fast cell provides the vast majority of the current due to its lower resistance. Following capacitor charging, the fast cell is recharged from the dense cell at a rate limited by the voltage difference between the cells.

20 Claims, 4 Drawing Sheets

HYBRID BATTERY NETWORK FOR IMPLANTABLE MEDICAL DEVICE

FIELD OF THE INVENTION

This invention relates to electronic components for implantable medical devices, and more particularly to batteries for implantable cardioverter/defibrillators.

BACKGROUND OF THE INVENTION

Implantable Cardioverter Defibrillators (ICDs) are implanted in patients susceptible to cardiac tachyarrhythmias including atrial and ventricular tachycardias and atrial and ventricular fibrillation. Such devices typically provide cardioversion or defibrillation by delivering low voltage pacing pulses or high voltage shocks to the patient's heart, typically about 500–800V. The ICD operates by detecting a fast heart rate or tachyarrhythmia, upon which a battery within the device housing is coupled via an inverter to a high voltage capacitor or capacitor pair to charge the capacitors. When the capacitor reaches a desired voltage, charging is stopped and the capacitors are discharged under control of a microprocessor to provide a therapeutic shock to the patient's heart.

While transcutaneous rechargeable battery systems have been contemplated, for example as provided in U.S. Pat. No. 5,991,665 to Wang et al., such a system has never been implemented in an ICD because of the lack of an acceptable battery recharging system. Therefore, it is generally expected that the battery must store all the energy needed for continuous monitoring and analysis of sensed electrogram and other physiologic signals, for telemetric communications and for potentially numerous shocks over the life of the device, and must retain the energy with minimal leakage to provide a long "shelf life" of at least several years, even if not frequently employed for shocks during its life. Thus, the energy storage capacity of the battery is important.

In addition, a battery must be capable of high current rates needed to charge the high voltage capacitors in a short time, so that a therapeutic shock may be delivered within a short time interval after the device has detected and diagnosed a need for the shock. If the battery has an excessive internal resistance, the current flow rate will be limited, delaying capacitor charging. This may result in syncope, ischemia (oxygen starvation) of critical organs and tissues. As a general principle, the sooner the therapy can be delivered following a detected episode, the better prospects are for the patient's health. In addition, it is believed that therapy delivered more promptly requires a lower energy therapy, allowing the conservation of the battery's energy to extend the device life before replacement is required.

Also, an omnipresent concern with implantable devices is device volume. A small device permits more flexibility in implant location, and provides improved patient comfort. There is generally a trade-off between size and storage capacity, with larger batteries providing more capacity. To mitigate this trade-off, batteries with high energy density (watt-hours per unit volume) are desired.

However, there is a trade-off between energy density and the current flow rate discussed above. The highest density cells, such as Mercury-zinc and Silver-zinc types are suited to applications where a moderate current draw occurs, but these have a high internal resistance that prevents them from providing the high current flow rate needed for rapid capacitor charging.

Thus, ICD designers have adopted low internal resistance battery chemistries such as Lithium Silver Vanadium Oxide (SVO), using one or more such cells. These provide the required rapid capacitor charging, but at the cost of somewhat compromised energy density. In addition, SVO and comparable performance batteries are expensive compared to other battery chemistries that lack only the needed current output. Also, over the life of existing devices, as SVO battery voltage diminishes, the time interval between diagnosis of an arrhythmia and completion of capacitor charging increases, so that the effective device life is limited due to the concerns noted above about delayed treatment.

In the past, certain implantable defibrillators were designed to reduce the demand on the battery used for critical, high current charging duties by employing a separate second cell having higher energy density and lower current capacity. This high density cell serves device circuitry not requiring high current rates, reducing the depletion of the lower energy density cell devoted to capacitor charging. While this may permit a slightly extended life, or slightly reduced size, the benefits are limited, because the low current battery circuitry adds size, complexity, and introduces a parasitic current load that will tend to reduce longevity.

SUMMARY OF THE INVENTION

The disclosed embodiment overcomes the limitations of the prior art by providing a battery network for an implantable cardiac stimulation device having first and second batteries with different battery chemistries connected in parallel with each other. The first battery has a higher resistance and a greater energy density than the second battery, and the second battery has greater current carrying capability than the first battery. Defibrillator circuitry is connected to the batteries. In a preferred embodiment, the first battery has a higher voltage than the second battery, and the second battery has a lithium anode. The device operates by detecting a need for treatment, providing current flow primarily from the second battery to the defibrillator circuitry, then providing current flow from the first battery to the second battery.

DETAILED DESCRIPTION OF A PREFERRED EMBODIMENT

Figure 1:
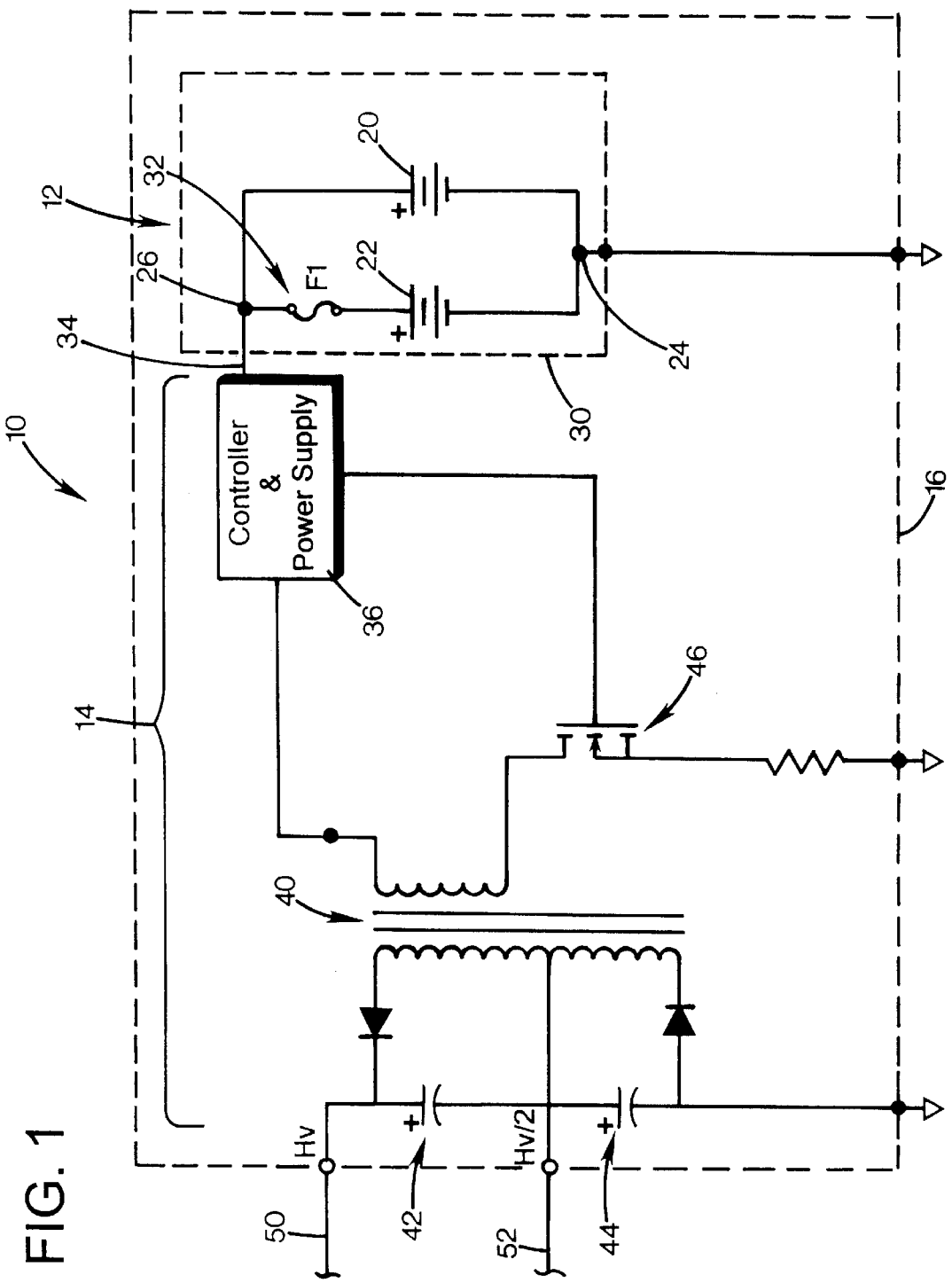
FIG. 1 is a schematic block diagram of an implantable defibrillator according to a preferred embodiment of the invention.

FIG. 1 illustrates an implantable cardioverter/defibrillator (ICD) 10 containing a battery network 12 connected to conventional defibrillator circuitry 14, all contained in a metallic conductive housing 16. The battery network 12 includes a first or "dense" cell 20 and a second or "fast" cell 22 connected in parallel between a ground node 24 and an output node 26, with the battery cathodes connected to the ground node, and the anodes connected to the output node. The ground node is connected to or provided by a conductive metal battery housing 30, which is electrically connected to the device housing 16, which serves as the device ground, and is in electrical contact with a patient in whom it is implanted. An optional current limiting device 32 such as a fuse is connected in line between the fast cell 22 and the output node 26. The cells are connected directly in parallel to each other (the current limiting device merely providing an ohmic connection in normal operating conditions), without any intervening electronic devices such as switches or regulating devices to increase cost, complexity, and/or size. The batteries may be provided as cells in separate compartments of the battery housing 30 or may be provided as separate batteries, each with its own housing.

The battery output node is connected to the circuitry 14 via an output line 34 extending through a sealed passage in the battery housing, and is electrically insulated from the housing. The circuitry 14 includes a controller and power supply 36 having a power input connected to the battery output line 34, and includes circuitry needed for pacing, arrhythmia detection, and other needed device functions. The controller has a power output connected to a DC-to-DC voltage converter 40, which is connected to a pair of high voltage capacitors 42, 44. A switching output of the controller is connected to the gate of a FET 46 connected between the converter and ground, so that a pulsing current may be used to generate a high voltage to charge the capacitors. In the preferred embodiment, with battery voltages of about 3V, a potential of up to 800V is developed across the pair of capacitors. A lead (not shown) extends to the patient's heart from a connector (not shown) in a header (not shown) of the ICD. The connector is coupled to the high voltage capacitors 42, 44 via lines 50, 52 and a high voltage output circuit (not shown).

In the preferred embodiment, the dense cell 20 is a Lithium Carbon Monofluoride cell such as are available from Wilson Greatbatch, Ltd. of Clarence, N.Y. with an open circuit voltage of 3.4V at its beginning of life (or discharge), and a theoretical capacity of 1.0–1.5 Amp-hrs. This chemistry has the desired qualities of minimal leakage for a long shelf life, a flat discharge curve that maintains an adequate voltage while its energy is consumed during its useful life, and has a relatively low mass density. The volume of the cell is 3 cc, and the energy density is about 1.3 W-hr/cc. Alternative battery chemistries providing adequate energy density include Mercury-zinc and Silver-zinc and any comparable chemistry existing or yet to be developed with the general characteristics and qualities of relatively high energy density, a relatively low internal resistance, high cathode efficiency, a flat discharge curve, and relatively low mass density. Any chemistry having an energy density of greater than 1.0 W-hr/cc may be considered, as long as it has suitable "dense cell" qualities noted above.

The dense cell has an internal resistance of 20–400 ohms, with 50 ohms being preferred. A resistance below this range would yield an excessive rate at which the dense cell recharges the fast cell after depletion, as will be discussed below, wasting heat energy and potentially causing damage. A resistance above this range would yield an excessive time to recharge the fast cell, undesirably delaying the delivery of a subsequent therapy.

The fast cell 22 is preferably a Lithium Silver Vanadium Oxide cell such as are available from Wilson Greatbatch, Ltd. of Clarence, N.Y. with a volume of 3 cc, and an open circuit voltage of 3.2V at its beginning of life (or discharge), which is slightly less than that of the dense cell. Because the dense cell has a higher voltage under all operating conditions throughout the device life, it will serve to charge the fast cell when the fast cell is occasionally used for capacitor charging and at least partially depleted, as will be discussed below. The voltage difference between the cells is limited to a small fraction of their voltages so that the charge rate is limited to prevent overheating and damage while recharging the fast cell. Also, the small voltage difference is preferably about 0.3–0.4V, which leads to a desirable trickle charge or topping off of the fast cell by the dense cell when the fast cell has been used. As noted above, the limited voltage difference provides an inherent current limitation between the cells, so that undesirable current or voltage regulation components are not needed, and the cells may simply be hardwired in parallel to each other as shown.

In the preferred embodiment, the fast cell has an open circuit voltage 94% of that of the dense cell, although this number may range between 70% and 95%. The fast cell has a loaded voltage of 2.5V, which is the approximate voltage when the cell is connected to the low resistance load of the DC-to-DC converter.

The fast cell has a theoretical capacity range of 0.3–0.7 Amp-hrs, which is less than that of the dense cell by a factor of 1.4 to 5.0. While some advantages of the invention may be achieved with a dense cell having a capacity less than or equal to that of the fast cell, the cost, size, and product life advantages are best served by a dense cell with greater capacity than the fast cell. The fast cell need only have adequate capacity to provide energy for 10 to 30 capacitor charges; the dense cell is sized with a capacity to serve an expected life, both in terms of shelf life years, and in terms of a total number of therapy shocks delivered. The dense/fast capacity ratio may be increased for applications in which a very long product life is required (and increased size is tolerated), or for devices using lower-energy therapy techniques. The ratio may be smaller for devices needing only a limited life, where smaller device size is needed, and/or where therapy requires greater energy discharge.

The fast cell has an internal resistance of 0.5–3.0 ohms, which is less than that of the dense cell by a factor in the range of 17–1000, leading to a corresponding difference in current flow rate capability under a comparable load. In the preferred embodiment, this resistance ratio is in the range of 20–100, and 40 is considered optimal. In the preferred embodiment, the resistance of the fast cell changes tolerably over the device life, beginning at 0.8 ohms, reducing to 0.5 ohms in the middle of life, and increasing above 1.0 ohms at the end of life.

Alternative fast cell chemistries include Lithium Ion with a Cobalt-based cathode, and any comparable chemistry existing or yet to be developed with the general characteristics and qualities of very low internal resistance yielding a high current carrying capability, an energy density that is about one half that of the dense cell's, and a low leakage rate.

In the preferred embodiment, the fast cell has a lithium anode, while the alternative embodiment discussed below has a fast cell with a lithiated carbon anode. Historically, Lithium Silver Vanadium Oxide cells have been used in implantable defibrillators due to their high current carrying capability. However, recharging cells with lithium anodes has previously been avoided in many applications, for the following reasons. Cells with lithium anode technology are relatively expensive, are used in very special applications, and are not readily adopted when well known and characterized technologies are desired. In addition, lithium anode technology could be potentially dangerous in some applications, because recharging of such a cell at excessive rates can cause overheating and explosion. Thus, the recharging of lithium anode cells has been avoided for use in implantable medical devices due to the possible risk. However, the preferred embodiment inherently avoids the risk of overcharging by using one battery (of limited voltage and current) to charge the fast cell. There is no way for the fast cell to receive a higher voltage than is provided by the dense cell, unlike other applications where a charge rate regulator may fail and lead to damage or injury.

Figure 2:
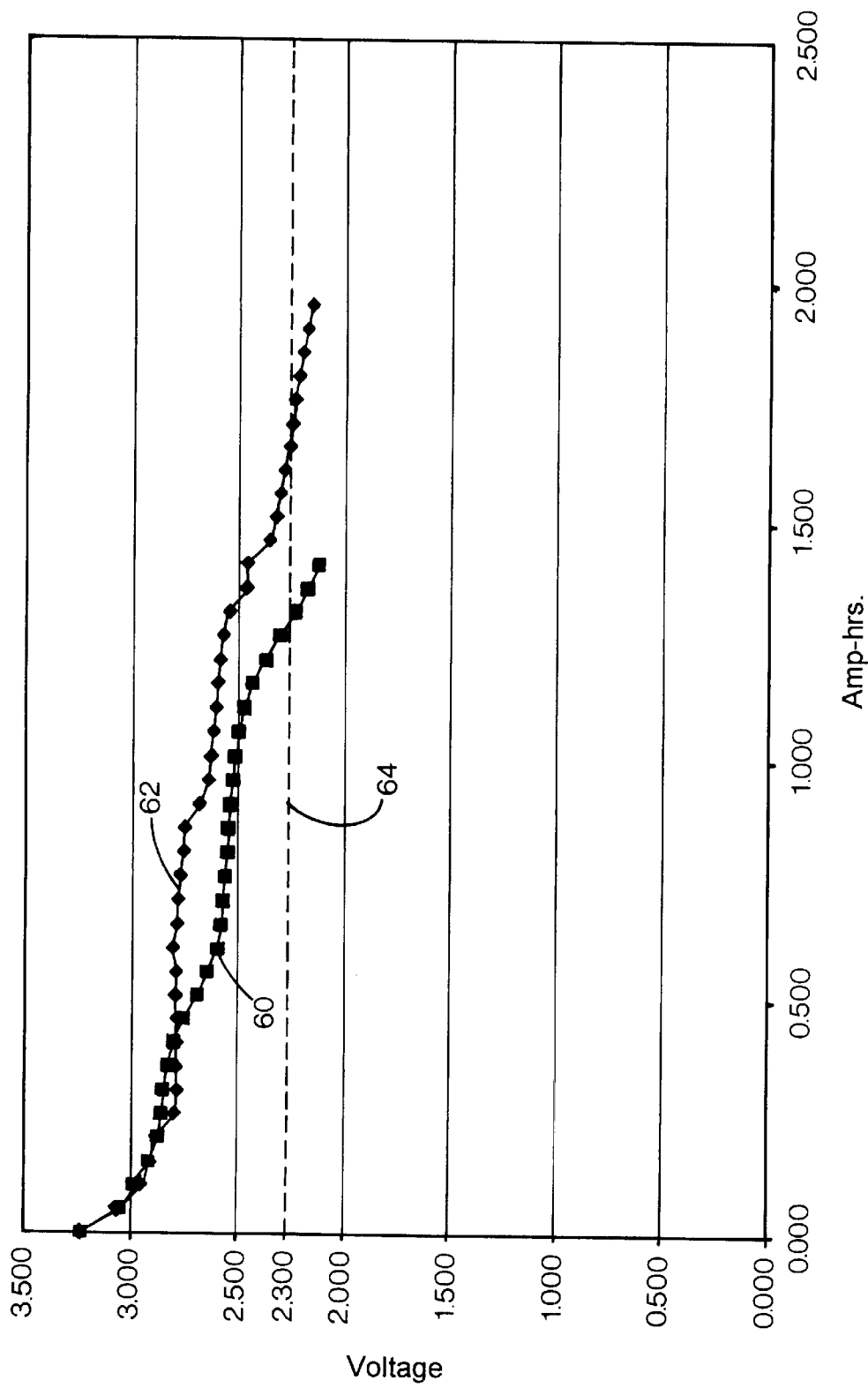
FIG. 2 is a graph illustrating operating performance of the preferred embodiment in comparison to a prior art device.

FIG. 2 illustrates the performance difference between the preferred embodiment system using the different battery chemistries, and a prior art conventional battery system using two identical SVO or fast cells. The tested battery systems have essentially the same volume of (3+3=6)cc, so that performance differences are attributable to the chemistry differences and not size. For each battery, the experiment was conducted by repeatedly placing a load on the batteries, causing them to charge a capacitor circuit as in an actual device. Such a charge is drawn every two hours during the experiment, and lasts 10 to 30 seconds, with the batteries being dormant for most of the two-hour period. The indicated voltage is the open circuit voltage measured prior to a capacitor charge, and not during the time the load is applied.

Line 60 indicates the prior art dual-SVO battery, and line 62 indicates the hybrid battery of the preferred embodiment; the voltage is indicated on the vertical axis, and power consumed (in Amp-hrs) is indicated on the horizontal axis. The total energy delivered is indicated by the area under each curve. An open circuit voltage threshold of 2.3V is indicated by threshold line 64. This threshold is considered the minimum voltage needed by the battery to charge the capacitors in a suitably brief time of no more than 30 seconds after an arrhythmia is diagnosed. When the battery voltage has dropped below this level, the device is considered to be at the end of its useful life, and is due for replacement.

As indicated, the preferred embodiment indicated by line 62 has an operating life greater than the prior art battery indicated by line 60, and drops below the voltage threshold at about 1.6 amp-hours as compared to 1.25 amp-hours for the dual SVO device. Thus, in a package of the same size, product life is extended by about 30%. In addition, it is notable that the slope of the line 62 as it passes below the threshold is gentler than that of the prior art line 60 as it passes below the threshold, indicating that where lower thresholds are tolerated, the difference in life becomes even greater.

The illustrated experiment is very conservative, and is more demanding than normal usage. It simulates a patient receiving the delivery of therapy every two hours for a period of weeks, which would be an extraordinary medical circumstance. More typical usages involve extended periods of days, weeks, months, or years between therapy events, allowing the cells to fully recover and equilibrate in a manner that is believed to increase the performance life differences between the two tested battery configurations. The capacitor charge duration varies only minimally as needed to ensure a full charge, with charges late in a battery's life taking slightly longer. For clarity, it is important to note that the batteries are not charged; the "charging" referred to herein is the charging of the capacitors, caused by discharging of the batteries.

Figure 3A:
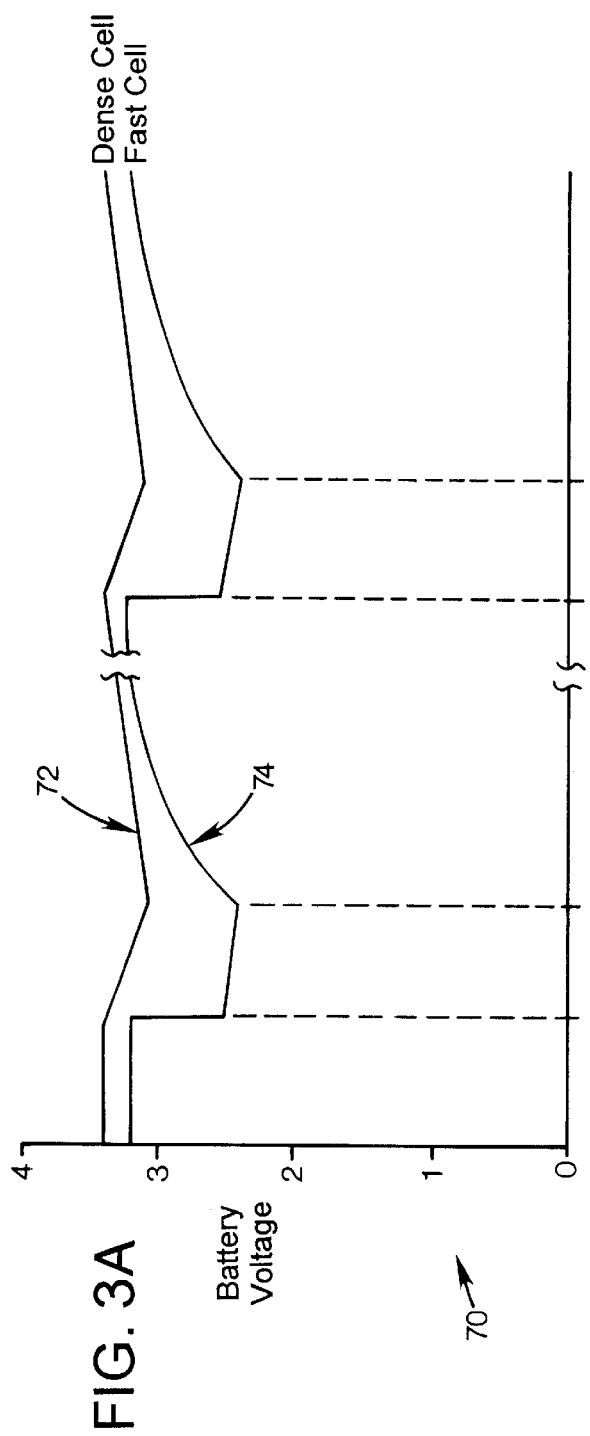
FIGS. 3A and 3B are a timing diagrams illustrating operation of the preferred embodiment.
Figure 3B:
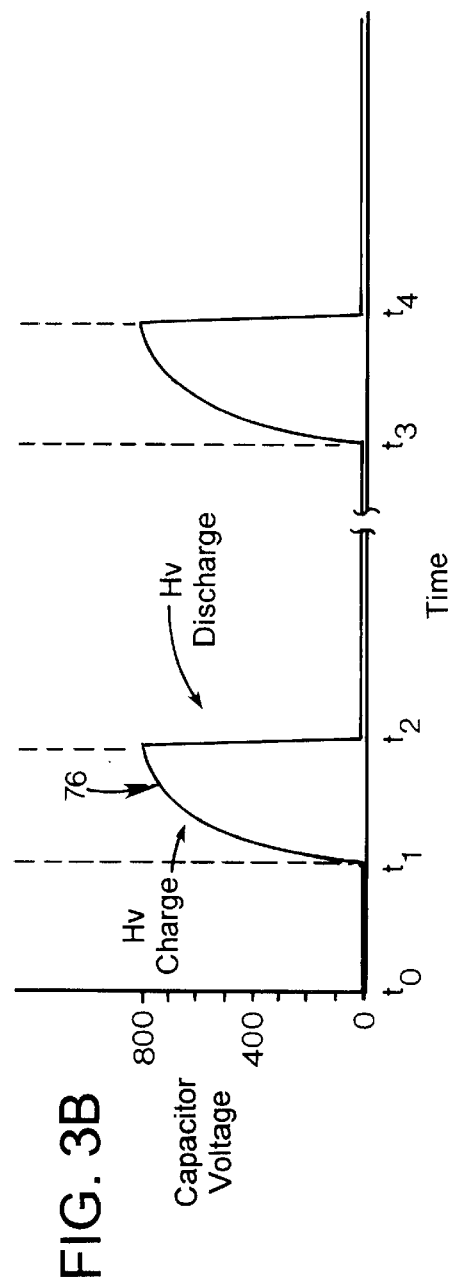

FIG. 3 shows a timing diagram 70 of the operation of the preferred embodiment of the invention during two incidents of high voltage capacitor charging and discharging to provide therapy for an arrhythmia. The diagram has an upper part indicating the voltages of the batteries over time, and a lower part indicating the capacitor voltage over the same time scale. Line 72 indicates the voltage across the dense cell 20, line 74 indicates the voltage across the fast cell 22, and line 76 indicates the voltage potential of the output line 50. Critical moments in time are indicated by $t_0$, $t_1$, $t_2$, $t_3$, and $t_4$.

During the $t_0$–$t_1$ interval, the batteries are at their open circuit voltages indicated above, with the dense cell's slightly greater voltage providing a continual topping off of the fast cell to ensure that the fast cell is maximally saturated. The capacitor is at zero voltage, avoiding the leakage of charge to which capacitors are typically vulnerable. At $t_1$, the controller has detected an arrhythmia and determines that therapy is needed. It immediately connects the output node 26 of the batteries to the converter 40, and cycles the FET 46 to initiate pulsed current flow to charge the capacitors.

The fast cell immediately experiences a voltage drop to its loaded voltage of about 2.5V, and during the $t_1$–$t_2$ interval provides the bulk of the current to the load at about 2.0 A for about 10 seconds. In response to the initial voltage drop across the fast cell, the dense cell voltage begins to drop gradually, as current slowly flows from the dense cell to the fast cell and to the load, at a rate limited by the high internal resistance of the dense cell. During this charging interval, the capacitors are charged to a total voltage of 750–800V, and the voltages of both cells diminish slightly under the charging load.

At time $t_2$, the controller has detected that the capacitors are fully charged, and disconnects the batteries from the converter. The high voltage capacitors are then caused to deliver their charge to the patient's heart via the leads. In practice, the discharge of the high voltage capacitors is a truncated exponential biphasic waveform that is delivered leaving about 100 to 200 V on the capacitors. This voltage then bleeds off over time or is the starting point for the next charge if another shock is needed to terminate the arrhythmia. However, for illustrative purposes the voltage is shown in the figure as dropping to zero. The controller thus ceases the charging operations at $t_2$, and the cells are returned to a open circuit voltage. During the ensuing $t_2$–$t_3$ period, the primary activity is the flow of current from the dense cell to the fast cell, initially at a rate of about 2 mA, and gradually diminishing. This recharges and readies the fast cell for the next possible therapy delivery. During this period, the fast cell voltage rises at a rate proportional its voltage difference from the dense cell, due largely to the recharging effect of the dense cell, but also because of voltage recovery as the load is eliminated. The dense cell voltage also recovers slightly in spite of the load of charging the fast cell.

This recharging interval may vary widely in duration. In unusual circumstances, a patient may experience a ventricular tachycardia "storm" requiring about 10–15 therapy shocks in a short period. The fast cell may provide this need without significant recharging, except that as its voltage drops, the time needed to recharge the capacitors increases. In normal circumstance in which there is a significant interval of hours or more between events, the dense cell can fully recharge the fast cell. This permits a fast response to the next detected arrhythmia, reducing syncope concerns. With normally long recharging intervals, the fast cell can remain ready at nearly its maximum voltage for the next event, so that therapy may be delivered promptly. The dense cell is selected to provide a typically flat voltage output over its life, so that as it is depleted, the fast cell may be recharged to nearly the same voltage as when the cells were fresh. Further, even if the dense cell were to diminish in voltage over time, this would not have a significant effect on the $t_1$–$t_2$ interval, but would only extend the $t_2$–$t_3$ interval, which is less medically critical in most instances. At time $t_3$, another arrhythmia is kiagnosed, and the cycle is repeated.

In the preferred embodiment, the cells would be contained in a single metal housing having two chambers, with the chambers sealed with respect to each other to isolate the different battery chemistries. This essentially provides a hybrid or composite battery with a compact package, and allows a short current path between the cells.

Figure 4:
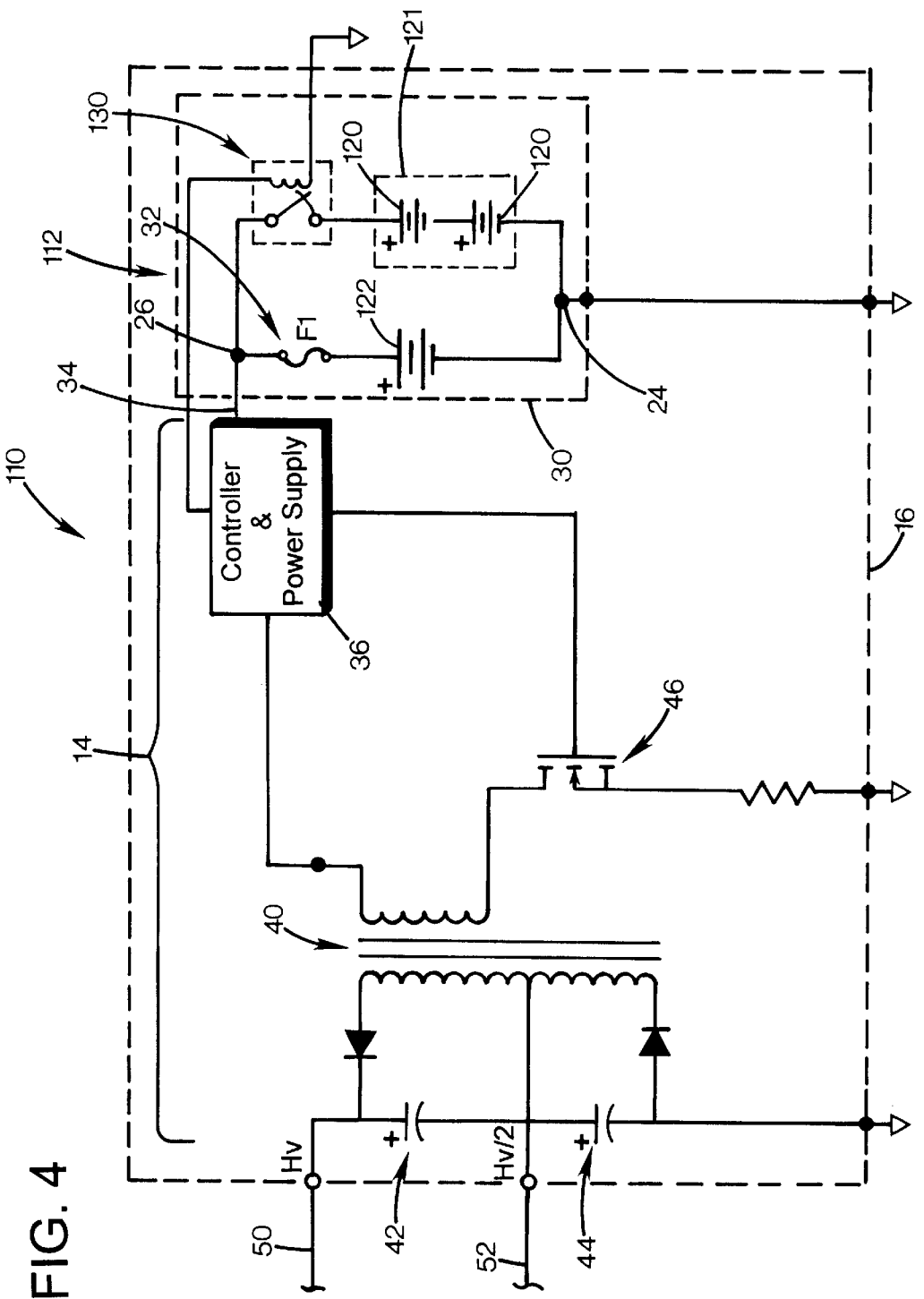
FIG. 4 is a schematic block diagram of an implantable defibrillator according to an alternative embodiment of the invention.

FIG. 4 illustrates an alternative implantable cardioverter/defibrillator (ICD) 110 containing a battery network 112 having a fast cell 122 connected in parallel with a dense cell set 121. The fast cell is a Lithium Ion rechargeable cell with a carbon anode having a volume of 3 cc and an open circuit voltage of 4.1 volts when fully charged, and with the same current rating and other characteristics as the SVO in the preferred embodiment discussed above. The dense cell set 121 includes two Lithium Carbon Monofluoride (LiCF$_x$) cells 120 (dense cells) connected directly in series to each other, the cathode of one connected directly to the anode of the other. Each dense cell 120 is about half the volume of the dense cell discussed above with respect to FIG. 1, and the set has a total open circuit voltage of 6.8V, significantly higher than that of the fast cell.

A normally closed relay 130 is serially connected between the dense cell set and the output node 26, with a control line operably connected to the controller, and a ground line. The relay is operated selectively by the controller to be open when the output node is at a voltage above a threshold of 4.1V, and to close when the output node voltage is below the threshold. The relay opens and removes the LiCFx apparent cell from the circuit at 4.1V, and closes to include the LiCFx apparent cell in the circuit when the voltage drops below 3.8V. This permits rapid charging of the fast cell by the dense cell set immediately when a capacitor-charging load is placed on the fast cell. By opening the circuit after the fast cell is adequately charged and ready for the next event, leakage from the dense cell is prevented, and its energy is conserved. In addition, the significant voltage differential of 1.0V may allow fast recharging of the fast cell, while the ability to disconnect the dense cell prevents overcharging and the attendant energy loss.

An added benefit of the alternative embodiment of FIG. 4 is that any unavoidable leakage current from the always-connected fast cell 122 is not wasted, but is used by the system to operate the ongoing background functions of the controller and other device circuitry.

While described in terms of a preferred embodiment, the invention need not be so limited.

What is claimed is:

1. An implantable cardiac stimulation device comprising:
   a first battery having an anode and a cathode;
   a second battery having an anode and a cathode and electrically connected in parallel to the first battery;
   the first battery having a higher resistance and a greater energy density than the sceond battery;
   a charging circuit connected to the batteries;
   the anodes of the first and second batteries being directly connected to each other; and
   the cathodes of the first and second batteries being directly connected to each other.

2. The device of claim 1 wherein said device is an implantable defibrillator and further includes a capacitor connected to the batteries via the charging circuit.

3. The device of claim 1 including a housing containing the batteries in separate compartments.

4. The device of claim 1 wherein the first battery has a higher voltage than the second battery.

5. The device of claim 1 wherein the second battery has an active lithium anode.

6. The device of claim 1 wherein the second battery is a Lithium Silver Vanadium Oxide cell.

7. The device of claim 1 wherein the first battery is a Lithium Carbon Monofluoride cell.

8. The device of claim 1 wherein the first battery has an amp-hour capacity greater than the amp-hour capacity of the second battery.

9. The device of claim 1 wherein the second battery has a current rating of at least 10 times that of the first battery.

10. A long-life high speed battery network comprising:
    a first battery having an anode and a cathode;
    a second battery having an anode and a cathode and electrically connected in parallel to the first battery;
    the anodes of the batteries being directly connected to each other, and the cathodes of the batteries being directly connected to each other;
    the first battery having a higher resistance and higher open cell voltage than the second battery; and
    the second battery having a greater current carrying capability than the first battery.

11. The network of claim 10 wherein at least one of the first and second batteries has an active lithium anode.

12. The network of claim 10 wherein the first battery has an amp-hour capacity of at least double the amp-hour capacity of the second battery.

13. The network of claim 10 wherein the second battery has a current rating of at least 10 times that of the first battery.

14. The battery network of claim 10 wherein said first battery and second battery form a composite battery comprising a battery housing having first and second compartments with said first and second batteries positioned respectively in said first and second compartments.

15. An implantable defibrillator comprising:
    a battery set comprising first and second batteries each having an anode and a cathode, the first and second batteries connected in series with the anode of one of the first and second batteries connected directly to the cathode of the other of the first and second batteries;
    a third battery electrically connected in parallel to the battery set;
    the battery set having a higher open circuit voltage and higher resistance and a greater energy density than the third battery; and
    a charging circuit connected to the batteries.

16. The implantable defibrillator of claim 15 and further including a relay coupled between the anode of the battery set and a node coupled to the anode of the third battery.

17. The implantable defibrillator of claim 16 and further including a controller coupled to the relay for disconnecting the battery set from the node when voltage at the node exceeds a predefined threshold.

18. The implantable defibrillator of claim 15 wherein the first and second batteries are Lithium Carbon Monofluoride cells.

19. The implantable defibrillator of claim 15 wherein the third battery is a Lithium Ion rechargeable cell having a carbon anode.

20. The implantable defibrillator of claim 15 wherein the third battery has an anode and a cathode, and wherein the anode of the third battery is connected directly to the anode of one of the first and second batteries, and the cathode of the of the third battery is connected directly to the cathode of one of the first and second batteries.

* * * * *